(12) United States Patent
Benjamin et al.

(10) Patent No.: US 7,424,821 B1
(45) Date of Patent: Sep. 16, 2008

(54) CHARACTERIZATION OF POROUS MEDIA

(75) Inventors: Grant S. Benjamin, Ingleside, IL (US);
Daniel R. Boggs, Libertyville, IL (US);
Rosa H. Yeh, Libertyville, IL (US)

(73) Assignees: Baxter International Inc., Deerfield, IL (US); Baxter Healthcare S.A., Wallisellen, Zurich (CH)

( * ) Notice: Subject to any disclaimer, the term of this patent is extended or adjusted under 35 U.S.C. 154(b) by 0 days.

(21) Appl. No.: 11/158,771

(22) Filed: Jun. 22, 2005

Related U.S. Application Data

(60) Provisional application No. 60/582,769, filed on Jun. 25, 2004.

(51) Int. Cl.
*G01N 5/02* (2006.01)
(52) U.S. Cl. .......................................... 73/73
(58) Field of Classification Search ....................... 73/73
See application file for complete search history.

(56) References Cited

U.S. PATENT DOCUMENTS

| 4,880,548 | A | | 11/1989 | Pall et al. | |
|---|---|---|---|---|---|
| 4,976,861 | A | * | 12/1990 | Pall | 210/508 |
| 5,034,135 | A | | 7/1991 | Fischel | |
| 5,274,159 | A | * | 12/1993 | Pellerite et al. | 556/485 |
| 5,407,581 | A | * | 4/1995 | Onodera et al. | 210/654 |
| 5,616,254 | A | * | 4/1997 | Pall et al. | 210/806 |
| 5,804,280 | A | * | 9/1998 | Pall et al. | 428/137 |
| 5,900,270 | A | * | 5/1999 | Smith et al. | 427/8 |
| 6,565,748 | B1 | | 5/2003 | Wang et al. | |
| 6,908,553 | B1 | * | 6/2005 | Boggs et al. | 210/501 |

FOREIGN PATENT DOCUMENTS

| EP | 0 508 162 A1 | 10/1992 |
|---|---|---|
| EP | 0 508 162 B1 | 10/1992 |
| EP | 0 620 017 B1 | 9/2002 |
| EP | 1 238 694 A2 | 9/2002 |
| EP | 1 238 694 A3 | 9/2002 |
| WO | WO 00/54873 A1 | 9/2000 |
| WO | WO 2004/039474 A2 | 5/2004 |

\* cited by examiner

*Primary Examiner*—Hezron E. Williams
*Assistant Examiner*—Rodney T Frank
(74) *Attorney, Agent, or Firm*—Andrew G. Kolomayets; Braford R. L. Price

(57) ABSTRACT

Porous filter media and methods for characterizing, selecting and using such media based on their dynamic wettability are disclosed. The dynamic wettability of a medium is a measure of how quickly a given liquid is absorbed by the medium.

14 Claims, 2 Drawing Sheets

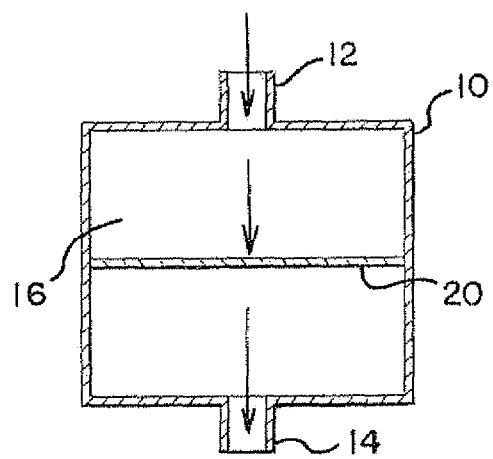
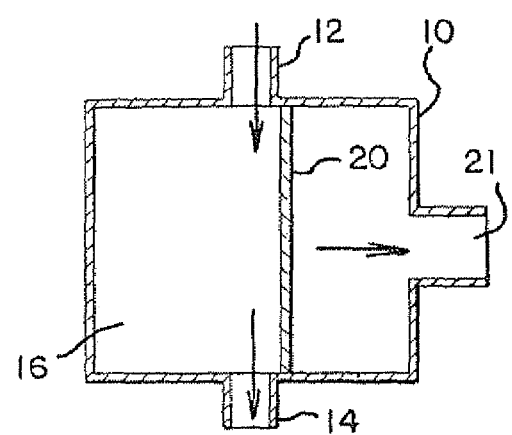
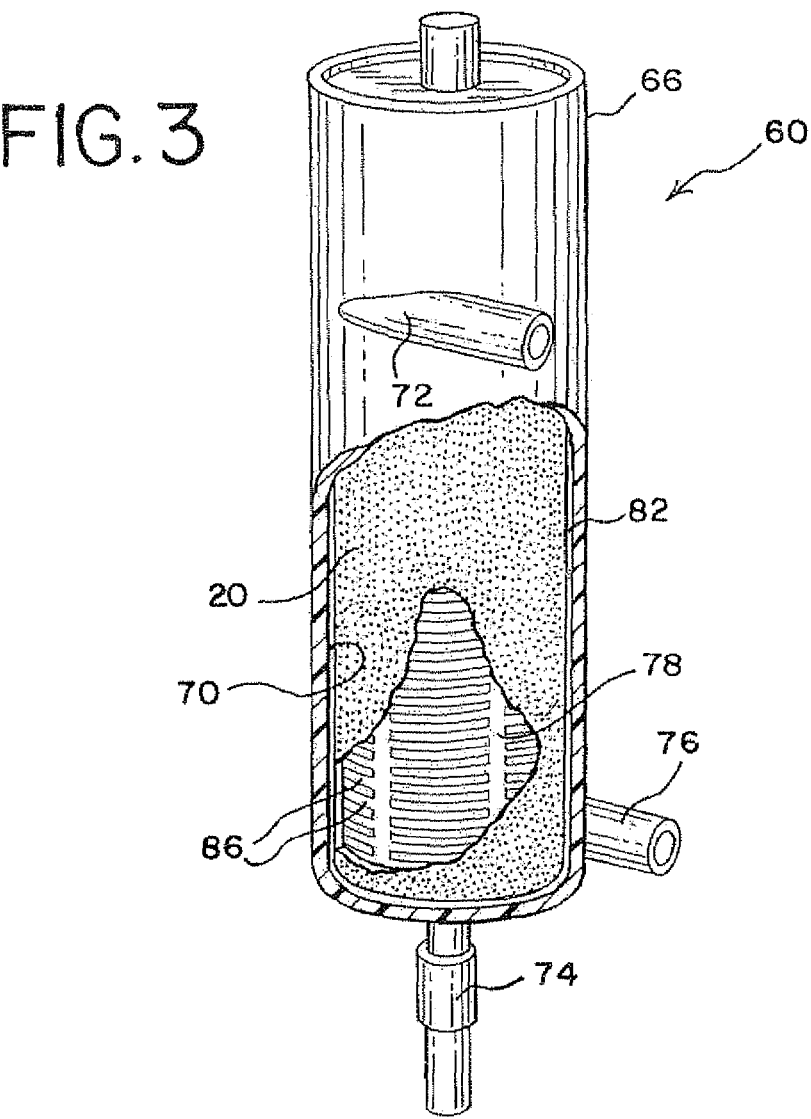

CHARACTERIZATION OF POROUS MEDIA

CROSS-REFERENCE TO RELATED APPLICATIONS

This application claims the benefit of U.S. Provisional Application No. 60/582,769, filed Jun. 25, 2004, the disclosure of which is hereby incorporated by reference in its entirety.

The present invention generally relates to porous media and methods for using such media. More particularly, the present invention relates to methods of characterizing porous media by determining their rate of wettability or dynamic wettability and selecting and using the porous media based on the dynamic wettability.

BACKGROUND OF THE INVENTION

Porous media are commonly used to filter, absorb, adsorb, separate, or otherwise remove selected components from a liquid. In the medical field, porous media are commonly used in the processing of biological fluids. For example, porous filter membranes have been used to separate components of biological fluid. One example of such an application is the Autopheresis-C® System sold by Baxter Healthcare Corporation, of Deerfield, Ill., the assignee of the present application. In the Autopheresis-C®, plasma is separated from the remaining blood components of a donor by passage through a spinning filter membrane. The plasma is collected for later processing and the other blood components are returned to the donor.

To be effective in the filtration, sorption, separation or removal of selected components from liquid, the porous medium must be "wettable" by the liquid with which the medium is in contact. "Wettability" is commonly determined by whether or not the liquid is absorbed by the porous medium. For example, a porous medium that, when contacted by a liquid, results in beads of liquid forming on the surface and remaining in bead shape is considered "not wettable" by the liquid.

Tests have been developed which characterize porous media in terms of whether or not they will be wet by a particular liquid. One way in which such media can be characterized is by their so-called "critical wetting surface tension," or CWST, described in detail in U.S. Pat. Nos. 4,880,548 and 4,976,861, assigned to the Pall Corporation and incorporated by reference herein. The CWST of a porous medium may be determined by individually applying to its surface, preferably dropwise, a series of liquids with surface tensions varying by 2 to 4 dynes/cm, and observing the absorption or non-absorption of each liquid. The CWST of a porous medium, in units of dynes/cm, is defined as the mean value of the surface tension of the liquid which is absorbed and that of a liquid of neighboring surface tension which is not absorbed.

It has generally been assumed that porous media with comparable CWST values will exhibit similar performance characteristics, such as the rate of liquid flow through the medium at a given trans-medium pressure. However, it has been observed that porous media made of the same materials with the same mean pore size, same thickness and same CWST do not always behave in the same way. For example, porous media with very similar, or even the identical characteristics described above, may display significant differences in the interaction of the medium and the liquid with which the medium is in contact. For example, as discussed in greater detail below, in the field of biological fluid processing, similar porous media may at times display differences in the flow and the flow rate of the biological fluid through the media.

Until now, these differences in characteristics (such as, but not limited to flow rate) have not been discernible by any known method of characterizing the porous medium, such as CWST or other known tests. Thus, it would be desirable to provide a method of characterizing porous media with more precision and thereby discern differences between the surface characteristics of comparable media. Furthermore, a method that can discern subtle differences in surface characteristics can be correlated to certain desirable or undesirable interactions with the subject liquid, allowing the end user to select one porous medium over another otherwise comparable medium.

SUMMARY OF THE INVENTION

In one aspect, the present invention is directed to a method for separating blood components with a biological filter membrane. The method includes providing a device having a fluid inlet, a fluid outlet, a flow path therebetween, and a porous biocompatible membrane suitable for contact with blood components between the inlet and outlet. The membrane is selected based on its dynamic wettability as determined by an observed rate of absorption of a liquid at a plurality of selected time intervals. The method further includes introducing a biological fluid including at least two blood components into the flow path and contacting the porous membrane with the biological fluid.

In a another aspect, the present invention is directed to a device for separating components from a biological fluid. The device includes a housing including an inlet port and an outlet port and a flow path therebetween. A porous biocompatible membrane suitable for contact with a biological liquid is located in proximity to the flow path. The membrane is selected on the basis of its dynamic wettability as determined by an observed rate of absorption of a liquid at a plurality of selected time intervals.

BRIEF DESCRIPTION OF THE DRAWINGS

FIG. 1 is a schematic view of a device including a porous medium of the present invention;

FIG. 2 is a schematic view of a different embodiment of a device with the porous medium of the present invention;

FIG. 3 is a perspective view of a separation device used in the separation of components of a biological fluid with a membrane of the present invention on the surface of a spinning rotor in the device;

DETAILED DESCRIPTION OF THE DRAWINGS

Figure 4:
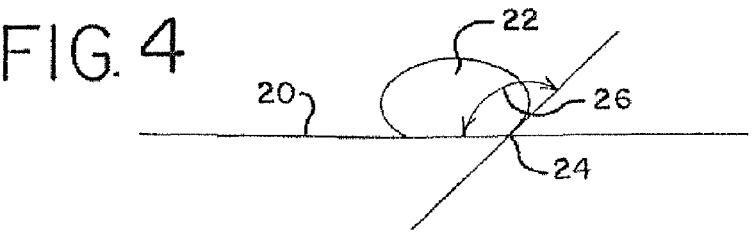
FIG. 4 is a schematic view of a drop of liquid on the surface of a porous medium of the present invention, showing a contact angle of greater than 90° between the medium surface and the drop.

Turning now to the figures, FIGS. 1 and 2 schematically depict devices in which porous media characterized and selected in accordance with the present invention may be used. As used herein, the terms "porous medium" or "porous media" include, but are not limited to, an article that has a porous structure and is capable of absorbing a liquid. It includes, but is not limited to media used for filtration, adsorption, absorption, or other forms of separation and/or removal of selected components from a fluid. Examples of porous media are membranes, such as fibrous screen membranes, cast membranes, track-etched membranes, sintered porous polymeric media, media with polymeric matrices with or without a particulate contained therein. Porous media include media used to separate blood components or blood fractions such as plasma from whole blood, or remove leukocytes from blood, or remove bacteria or other pathogens from a biological fluid, or remove compounds used in or resulting from a pathogen inactivation treatment from biological fluid. As defined, "porous medium" or "porous media" is not limited to membranes, polymeric filtration or removal media, but may include materials as diverse as wood, paper, concrete and the like. Nor is the term porous medium limited to articles for use in the medical field.

FIG. 1 generally shows a flow through removal or separation device. The device includes a housing 10 which has an inlet 12 through which a fluid is introduced and an outlet 14 through which the fluid exits. Housing 10 also includes an internal flow path 16 separated by a porous medium 20. Porous medium 20 may be a filter membrane characterized and selected in accordance with the present invention.

FIG. 2 shows an alternative embodiment of a flow through removal or separation device. In FIG. 2, medium 20 is disposed parallel to the direction of flow, thereby allowing fluid to contact the surface of the medium so that certain components pass through the device to outlet 14 while other components are blocked on the surface of the medium, and still other components optionally pass through outlet 21.

The devices shown in FIGS. 1 and 2 may be used for any application where filtration, separation or removal of components is desired. For example, in the area of biological fluid processing, the devices and more specifically, the porous medium therein, may be used to remove leukocytes from a leukocyte containing liquid (i.e., leukoreduction filter). The devices of FIGS. 1 and 2 with porous medium 20 may also be used to separate selected components from blood and/or to remove compounds used in the treatment of blood, such as pathogen inactivation compounds and by-products of a pathogen inactivation treatment.

FIG. 3 shows a more specific embodiment of a separation device wherein the porous medium is a filter membrane characterized and selected in accordance with the present invention. In the embodiment of FIG. 3, the membrane may be used in a disposable processing set for separating a biological fluid, such as blood, into its components. The separation device shown in FIG. 3, and the disposable set of which it is a part, are used with a device for separating whole blood into plasma and concentrated red cells, namely the Autopheresis-C® Plasmapheresis device sold by Baxter Healthcare Corporation. The structure and operation of the Autopheresis-C®, including the separator 60, are set forth in detail in U.S. Pat. No. 5,194,145, incorporated by reference herein, and the detailed description will not be repeated here.

Briefly, however, as depicted in FIG. 3, separator 60 includes a housing 66 defining a generally cylindrical inside surface 70. The housing includes a fluid inlet 72, a first outlet 74 and second outlet 76. A rotor 78, with a generally cylindrical outer surface, is rotatably mounted in the housing with the outer surface of the rotor spaced from the interior surface of the housing to define a small gap 82 therebetween. The membrane 20 of the present invention is placed on the rotor, with the membrane facing gap 82 located between rotor 78 and housing 66. The membrane rests atop a series of spaced-apart support ribs 86 on the surface of the rotor. These raised support ribs support the membrane and form channels to collect filtrate passing through membrane 20.

Although the membrane is shown on the surface of the rotor in FIG. 3, alternatively, the membrane may be mounted on the generally cylindrical interior surface of the housing or on both the rotor and housing. In that event, the surface of the housing may similarly include raised ribs to support filter membrane and to collect filtrate passing through the membrane.

In the separator 60 shown in FIG. 3, fluid such as a biological suspension or blood is introduced through inlet 72 and flows down through the gap 82 between the outer surface of the rotor 78 and inner surface of the housing 66. During the passage through the gap, the high-speed rotation of rotor generates turbulence in the form of Taylor vortices, which sweep the membrane free of clotting cells or debris. Assisted by substantial transmembrane pressure generated by flow control pumps, plasma from the blood passes through membrane 20 and is collected in the channels defined between the spaced apart raised ribs. The plasma flows down through the channels into a collection manifold, and passes through first outlet 74. The remaining portion of the fluid or suspension (e.g., concentrated cells) is withdrawn from the housing through the second outlet 76.

In a preferred embodiment, porous medium 20 may be a porous filter membrane made of a polymeric material. Optionally, the porous filter membrane may be made of a polymeric material coated on a polymeric support. Such membranes having a polymeric support and the methods of making them are well known in the art and will not be described in detail here. Briefly, however, polymeric support is coated with a polymeric coating solution. (The polymeric solution is the polymeric material dissolved in a solvent.) The support with the coating thereon is then contacted with a solution selected to precipitate parts of the polymeric coating solution (e.g., the solvent in which the material is dissolved), thus creating a porous surface. After any required rinsing, the membrane is dried, cut and/or applied to rolls.

The polymeric coating is one that is biocompatible, and capable of being sterilized by methods of sterilization typically used in the medical field. In one preferred embodiment, the coating on the support is made of a polyamide, such as nylon, and more preferably Nylon 66. Other materials can also be used to coat the polymeric support. For example, in one embodiment, polycarbonate may be used. In another embodiment, polyvinylidenedifluoride (PVDF) or other fluorinated polymers may be used. These membranes may be further treated or coated with solutions such as polyvinyl alcohol (PVOH) to affect their wettability.

The polymeric support can be any material that is compatible with the polymeric coating and one which the polymeric solution will effectively coat. In a preferred embodiment, the support may be a non-woven polymeric material. One example of a suitable support is a polyester mesh.

Membrane 20 will have a thickness and a mean pore size based on the desired separation procedure. For example, in an embodiment where membrane 20 is used to separate plasma from whole blood in a device such as the Autopheresis®, membrane 20 includes a nylon coating on a polyester support. The membrane (including the support) has a preferred thickness of approximately 0.0050-0.0075 inches and a nominal pore size of approximately 0.65 microns.

As discussed above, in accordance with one aspect of the present invention, membranes or other porous surfaces may be characterized in a way that has been previously unknown, namely, by observing and measuring their dynamic wettability. "Dynamic wettability," as used herein, means the rate at which a drop of liquid (with a surface tension that may or may not be known and a drop volume that is preferably known) is absorbed by the membrane or porous medium. The absorption is observed and measured at a plurality of selected time intervals, such as, but not limited to, every 30 seconds, every 45 seconds, every minute, etc.

Determining the dynamic wettability of a membrane or other porous medium can be carried out by any technique which allows one to determine the rate that the drop of liquid (with a surface tension that may or may not be known) is absorbed by the medium over a period of time. Determining dynamic wettability may include observing one or more physical characteristics of the drop or the porous medium that relates to absorption at a plurality of time intervals. Physical characteristics (and the changes thereto) that may be observed include, but are not limited to, the area of the drop, the height of the drop, the width of the drop, the diameter of the drop, the overall shape of the drop (i.e., a discrete circle or some other less regular shape), and/or the contact angle between the drop and the surface of the porous medium. In one preferred embodiment, determining the rate of absorption or dynamic wettability can be achieved by observing and measuring the contact angle (and the change thereto) of the liquid droplet on the surface of the medium, at a plurality of selected time periods. The results may be plotted to provide a visual assessment of the dynamic wettability (see FIG. 7 discussed below). This particular measurement offers a substantially precise way of determining the rate of absorption. Reduction in the contact angle over time can be measured by different techniques.

Figure 5:
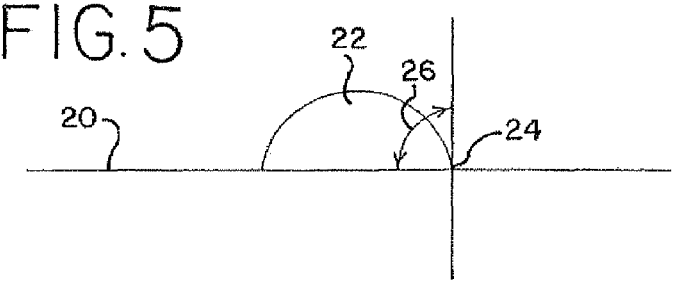
FIG. 5 is a schematic view of a drop of liquid on the surface of a medium showing a different contact angle (as compared to FIG. 1) between the medium with the drop.
Figure 6:
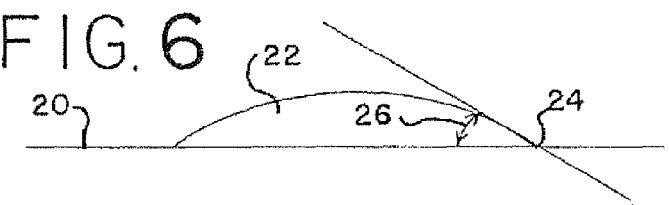
FIG. 6 is a schematic view of a drop of liquid on the surface of a medium showing a different contact angle (as compared to FIGS. 1 and 2) between the medium and the drop.

With reference to FIGS. 4-6, the contact angle, as used in the present application, is the angle 26, which is defined between the horizontal surface of medium 20 and the surface of the drop 22 at the point of contact as indicated by reference numeral 24 in FIGS. 4-6. As discussed above, measurements can be taken at selected time intervals. Using FIGS. 5-6 as an example showing the absorption rate of a liquid drop 22, FIG. 5 shows the contact angle of a drop 22 having a contact angle 26 that is approximately 90° (or less). At a later time period, the drop has been further absorbed, as evidenced by the further reduced contact angle. Thus, by measuring the reduction in the contact angle as a function of time, one can characterize the medium by its dynamic wettability.

Using the dynamic wettability of the medium, one can discern differences in the surfaces of otherwise seemingly similar or identical media. Based on the differences in the surface characteristics of the media, one medium can be selected over another medium for a particular application. In addition, dynamic wettability can be used to identify differences in the surface characteristics of a given porous medium, such as, for example, differences between different regions of the medium.

In one particular example of its application, dynamic wettability can be used to select a particular membrane over an otherwise comparable or substantially identical membrane for processing biological fluids through a device such as the Autopheresis-C®. More specifically, membranes providing a more consistent and less variable rate of plasma flow over time can be identified based on their dynamic wettability when compared to otherwise comparable membranes having a different dynamic wettability.

Figure 7:
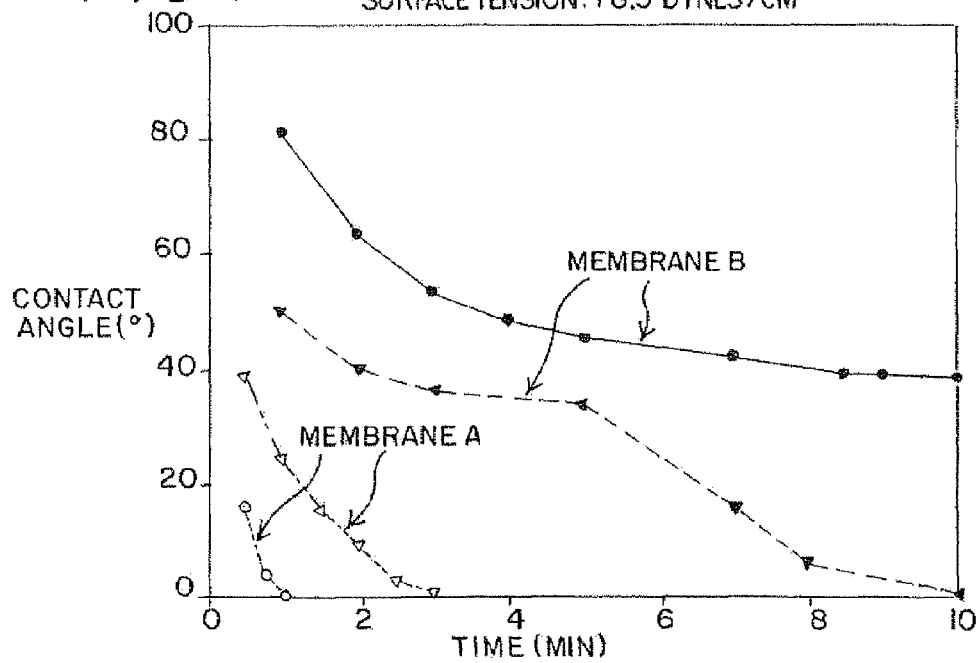
FIG. 7 is a graph comparing the dynamic wettability of two porous membranes having similar CWST, similar thicknesses and similar mean pore size.

Described below and shown in FIG. 7 is a comparative study wherein two membranes made of Nylon 66 on a polyester support, each having a thickness of approximately 0.0050-0.0075 inches, a nominal pore size of approximately 0.65 microns, and a CWST of approximately 78 dynes/cm were compared. Flow rate studies established that Membrane A had previously been identified as a membrane through which the flow rate of blood plasma (in a device such as shown in FIG. 3) diminished over time and there was evidence of platelet adhesion to the membrane surface. Membrane B was a membrane with a more consistent plasma flow rate (and less platelet adhesion).

Each of the sample membranes was cut into a strip. Drops of 17% NaCl solution having a surface tension of 78.5 dynes/cm were placed in the same locations on the respective strips (approximate size, 3/8 inch by 2 inch). A Model 100 Contact Angle Goniometer from Ramé-Hart was used to measure the contact angle of the drops at selected time intervals. Two samples from each membrane were tested. The results are set forth below and are graphically represented in FIG. 7.

| MEMBRANE A | |
| --- | --- |
| Contact Angle | Time (min.) |
| Sample 1 | |
| 16° | 0.5 |
| 4° | 0.75 |
| 0° | 1.0 |
| Sample 2 | |
| 39° | 0.5 |
| 24° | 1.0 |
| 15° | 1.5 |
| 9° | 2.0 |
| 2° | 2.5 |
| 0° | 3.0 |

| MEMBRANE B | |
| --- | --- |
| Contact Angle | Time (min.) |
| Sample 1 | |
| 81° | 1.0 |
| 63° | 2.0 |
| 53° | 3.0 |
| 48° | 4.0 |
| 45° | 5.0 |
| 42° | 7.0 |
| 39° | 8.5 |
| 39° | 9.0 |
| 39° | 10.0 |
| Sample 2 | |
| 50° | 1.0 |
| 40° | 2.0 |
| 36° | 3.0 |
| 34° | 5.0 |
| 16° | 7.0 |
| 6° | 8.0 |
| 4° | 10.0 |

As can be seen from the foregoing and from FIG. 7, the membrane with a slower or more moderate dynamic wettability was the membrane (Membrane B) displaying less variability in the plasma flow. Thus, in this example, dynamic wettability can be correlated to a specific biological interaction with the contacting liquid, and can be used to predict plasma flow properties and/or the likelihood of platelet adhesion to the membrane surface.

From the foregoing, it is clear that dynamic wettability can provide more precise information regarding how quickly a liquid is absorbed by a selected medium, thereby revealing sometimes subtle differences in the medium surface. The dynamic wettability can then be correlated to certain desirable or undesirable interactions with the contacting liquid and thereby allow selection of the medium based on the desirable or undesirable result. The dynamic wettability can also be used to characterize the capillarity of a given porous medium. The dynamic wettability can also be compared to the dynamic wettability of other comparable media and allow selection of a medium based on such comparison. In addition, the dynamic wettability of different areas of a given porous medium can be measured to identify the degree of uniformity in surface characteristics of a medium surface or, conversely, variables in the surface characteristics of the medium. This information can be useful, for example, in the area of manufacturing porous media. There may be other applications and used for dynamic wettability measurements.

The present invention has been described in the context of its preferred embodiments and end uses. However, using the dynamic wettability to characterize porous media may be useful in other applications. Accordingly, nothing in the foregoing description should be construed as limiting the invention to the examples and uses described above, and the true scope of the present invention is to be construed based on and limited only by the appended claims.

The invention claimed is:

1. A method for separating blood components with a biological filter membrane comprising:
   providing a device having a fluid inlet, fluid outlet, a flow path therebetween and a porous biocompatible membrane suitable for contact with blood components between said inlet and outlet wherein said membrane has been selected based on its dynamic wettability as determined by an observed rate of absorption of a liquid at a plurality of selected time intervals;
   introducing a biological liquid including at least two blood components into said flow path through said inlet;
   contacting said porous membrane with said biological liquid.

2. The method of claim 1 wherein said membrane has a dynamic wettability comparable to the dynamic wettability of a second porous membrane having a desired biological interaction with said biological liquid.

3. The method of claim 2 wherein said membrane has been selected on the basis of having a dynamic wettability that is slower than a dynamic wettability of a substantially identical second membrane.

4. The method of claim 1 wherein said liquid comprises blood plasma.

5. The method of claim 1 wherein including introducing said biological liquid into said flow path and passing at least some of said blood components through said selected membrane.

6. The method of claim 5 comprising passing at least blood plasma and platelets through said membrane.

7. The method of claim 1 comprising providing a membrane made of a polymeric material on a polymeric support.

8. The method of claim 7 wherein said polymeric material comprises nylon and said polymeric support comprises a woven polyester mesh.

9. The method of claim 2 wherein said desired biological interaction is a reduced level of platelet adhesion to the membrane surface.

10. A device for separating components of a biological liquid comprising:
    a housing including an inlet port and an outlet port and flow path therebetween;
    a porous biocompatible membrane suitable for contact with a biological liquid located in proximity to said flow path, wherein said membrane is selected on the basis of its dynamic wettability as determined by an observed rate of absorption of a liquid at a plurality of selected time intervals.

11. The device of claim 10 wherein said membrane has a dynamic wettability that is slower than a pre-determined faster dynamic wettability of a substantially identical second membrane.

12. The device of claim 10 comprising wherein said membrane is disposed within said flow path.

13. The device of claim 10 wherein said device further comprising a rotor within said housing including said membrane on the outer surface thereof.

14. The device of claim 10 including a porous membrane for separating white blood cells from blood.

* * * * *